United States Patent
Fang

(10) Patent No.: US 9,427,536 B2
(45) Date of Patent: Aug. 30, 2016

(54) ATOMIZER AND ELECTRONIC CIGARETTE USING THE SAME

(71) Applicant: Shenzhen Detail Technology Company, LTD., Shenzhen, Guangdong (CN)

(72) Inventor: Xiaolin Fang, Guangdong (CN)

(73) Assignee: SHENZHEN DETAIL TECHNOLOGY COMPANY, LTD., Shenzhen (CN)

( * ) Notice: Subject to any disclaimer, the term of this patent is extended or adjusted under 35 U.S.C. 154(b) by 0 days.

(21) Appl. No.: 14/678,937

(22) Filed: Apr. 4, 2015

(65) Prior Publication Data
US 2015/0305405 A1    Oct. 29, 2015

Related U.S. Application Data

(63) Continuation of application No. 12/831,553, filed on Jul. 7, 2010, now Pat. No. 9,022,026.

(51) Int. Cl.
 *A61M 15/06* (2006.01)
 *A24F 47/00* (2006.01)
 *A61M 15/00* (2006.01)

(52) U.S. Cl.
 CPC ............ *A61M 15/06* (2013.01); *A24F 47/008* (2013.01); *A61M 15/0021* (2014.02)

(58) Field of Classification Search
 CPC ............... A61M 15/06; A61M 15/00; A61M 15/0001; A61M 15/0021; A61M 15/0023; A61M 15/0086; A61M 15/009; A61M 15/0091; A61M 15/0095; A61M 11/00; A61M 11/04; A61M 11/041; A61M 11/042; A24F 47/002; A24F 47/00; A24F 47/004; A24F 47/008

USPC .......... 128/200.14, 200.24, 202.21, 204.13; 131/273, 374, 360
See application file for complete search history.

(56) References Cited

U.S. PATENT DOCUMENTS

| | | | | |
|---|---|---|---|---|
| 4,083,372 A * | 4/1978 | Boden | ................... | A24F 47/002 128/202.21 |
| 4,171,000 A * | 10/1979 | Uhle | ..................... | A61M 15/06 131/273 |
| 4,993,436 A * | 2/1991 | Bloom, Jr. | ............ | A24F 47/002 128/200.14 |
| 8,205,622 B2 * | 6/2012 | Pan | ........................ | A24F 47/008 131/273 |
| 8,375,957 B2 * | 2/2013 | Hon | ...................... | A24F 47/008 128/202.21 |
| 9,022,026 B2 * | 5/2015 | Fang | ..................... | A24F 47/008 128/202.21 |
| 2005/0016550 A1 * | 1/2005 | Katase | .................. | A24F 47/002 131/194 |
| 2006/0191546 A1 * | 8/2006 | Takano | ................. | A24F 47/002 131/270 |
| 2008/0092912 A1 * | 4/2008 | Robinson | .............. | A24F 47/008 131/200 |
| 2009/0126745 A1 * | 5/2009 | Hon | ...................... | A24F 47/008 131/273 |

* cited by examiner

*Primary Examiner* — Justine Yu
*Assistant Examiner* — Colin W Stuart
(74) *Attorney, Agent, or Firm* — Hemisphere Law, PLLC

(57) ABSTRACT

An electronic cigarette includes a container for storing a tobacco flavored liquid, an atomizer connected to the container to atomize the tobacco flavored liquid by an electric heating, a battery tube to power the atomizer, and an actuating film movably positioned in the battery tube to control the atomizer.

18 Claims, 3 Drawing Sheets

ATOMIZER AND ELECTRONIC CIGARETTE USING THE SAME

CROSS REFERENCE

This is a continuation of U.S. patent application Ser. No. 12/831,553, submitted on Jul. 7, 2010, entitled "Atomizer And Electronic Cigarette Using The Same", which has been allowed.

BACKGROUND

1. Technical Field

The present disclosure relates to electronic products, and particularly, to an atomizer and an electronic cigarette using the atomizer.

2. Description of Related Art

As is well known, smoking is not only harmful to a smoker, but also harmful to other people around him due to passive smoking, which is often referred as secondhand smoking. In addition, a lit cigarette end may cause a fire if it is not properly extinguished.

Therefore, there is room for improvement within the art.

DETAILED DESCRIPTION OF THE EMBODIMENTS

Figure 1:
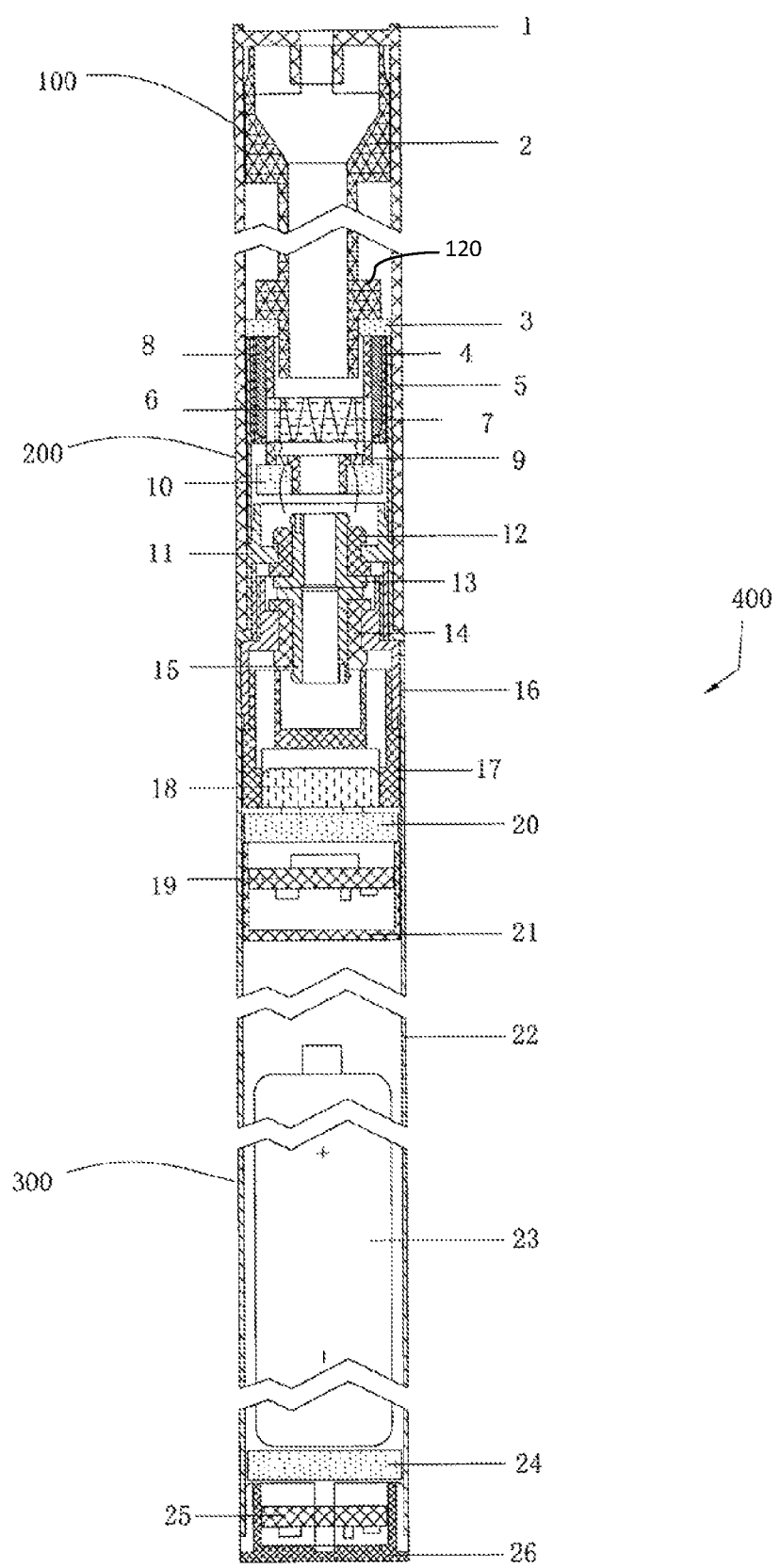
FIG. 1 is a cross-sectional view of an embodiment of an electronic cigarette.

Referring to FIG. 1, an embodiment of an electronic cigarette 400 includes a container 100 configured for storing a tobacco flavored liquid, an atomizer 200 configured for vaporizing the liquid by electric heating, and a battery tube 300 configured for powering the atomizer 200 and controlling the atomizer 200 to vaporize the liquid. The container 100, the atomizer 200 and the battery tube 300 are connected one by one.

Figure 2:
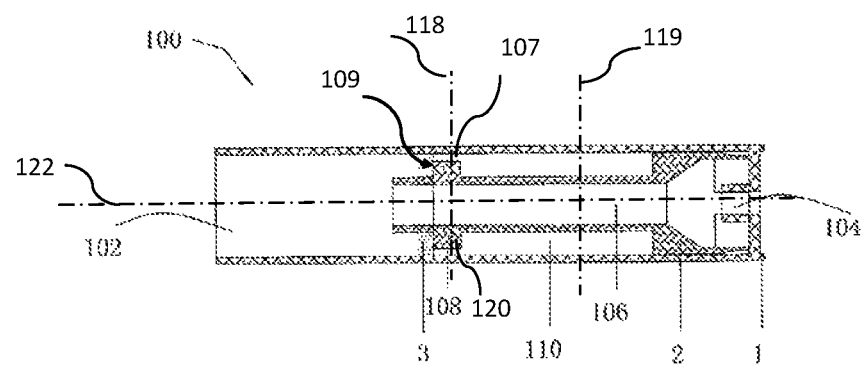
FIG. 2 is a cross-sectional view of an inhalation element of the electronic cigarette of FIG. 1.

Referring to FIG. 2, the container 100 is detachably connected to the atomizer 200 to facilitate replacement of the container 100 and the liquid. The container 100 is substantially hollow cylinder and includes an inhalation element 1, a liquid tank 2, an outlet-defining element 120 and an absorbent element 3. The inhalation element 1 is shaped as a substantially hollow cylinder defining an opening 102 at one end, and an inhalation hole 104 at the other end thereof as an inhalation end or a mouth-end piece. The liquid tank 2 defines a smoke channel 106 in a middle portion thereof communicating with the inhalation hole 104, in the embodiments of FIGS. 1 and 2, the liquid tank 2 is hollow cylindrical with the smoke channel 106 defined therein, and has concave or inward-curved out-surfaces. In the embodiments of FIGS. 1 and 2, the absorbent element is an exemplary annular and flange-shaped, and surrounds the smoke channel 106. The smoke channel 106 has a relative greater width in a portion adjacent to the inhalation hole 104, such that the atomized liquid fully contacts an inner wall of the liquid tank 2 and is cooled into water, thus avoiding the atomized liquid from affecting a taste of the liquid. The liquid tank 2 is received in the inhalation element 1 and contacts a sidewall of the inhalation element 1 with one end. The inhalation element 1, the liquid tank 2, outlet-defining element 120, and the absorbent element 3 cooperatively define a liquid storage cavity 110 to receive the liquid. The liquid storage cavity 110 has a liquid outlet 107. An outlet-defining element 120 is positioned at the liquid outlet 107, defines the shape of the opening of the liquid outlet 107, and reduces the size or sizes of an opening 108 of the liquid outlet 107. For instance, in the embodiment of FIG. 2, the outlet-defining element 120 is a flange-shaped structure extending into the liquid storage cavity 110, the liquid outlet 107 is reduced to a tubular passage for the opening 108 by the outlet-defining element 120, to such a degree that the opening 108 of the liquid outlet 107, on an intersecting planes 118 perpendicular to a longitudinal axis 122 of the container 100 at the opening 108 of the liquid outlet, has a smaller area than an area of the liquid storage cavity on an intersecting planes 119 perpendicular to the longitudinal axis 122 of the container 100 at a position of non liquid outlet portion of the liquid storage cavity 110. The liquid outlet 107 extends from the liquid storage cavity 110 to an outside end 109 of the outlet-defining element 120. The absorbent element 3, in the embodiment of FIG. 2, is attached to the outlet-defining element 120 at the outside end 109 to cover the opening 108 of the liquid outlet 107, yet allows the liquid to permeate through. Because the size or sizes 108 of the opening 108 of the liquid outlet 107 are limited by the outlet-defining element 120, the velocity of the liquid received in the storage cavity 110 flowing to the absorbent element 3 is slowed down due to smaller area of the opening 108 of the liquid outlet 107, such that a fast consumption of the liquid and a high concentration of the atomized flavored liquid can be avoid. The inhalation element 1 and the liquid tank 2 may be made of food-grade polypropylene (PP) and is disposable. In the illustrated embodiment, the absorbent element 3 is absorbent cotton.

Figure 3:
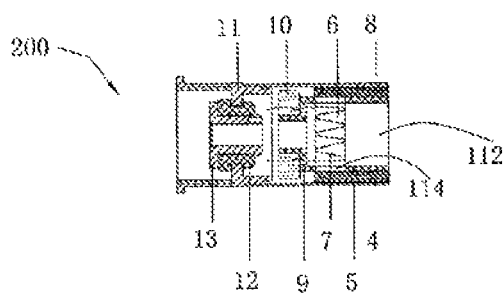
FIG. 3 is a cross-sectional view of an embodiment of atomizer of the electronic cigarette of FIG. 1.

Referring to FIG. 3, the atomizer 200 includes a liquid conducting element 4, a stainless steel pipe 5, a sleeve 6, a heating wire 7, a metal fiber element 8, an atomizing cup 9, a nonwoven fabric 10, a nut 11, a first washer 12, and a first pin 13. The stainless steel pipe 5 is closely attached to an inner sidewall of the inhalation element 1. The inhalation element 1, the stainless steel pipe 5, the liquid conducting material 4, the metal fiber element 8 and the atomizing cup 9 are coaxially arranged in that order. Both of an end of the liquid conducting material 4 and an end of the metal fiber element 8 contact the absorbent element 3. The atomizing cup 9 defines a cavity 112 in a middle portion thereof. The other end of the liquid tank 2 is received in the atomizing cup 9, such that the cavity 112 communicates with the smoke channel 106. The atomizing cup 9 defines two coaxial through holes 114 on a sidewall thereof communicating with the cavity 112. The sleeve 6 is received in the cavity 112 and aligned with the two through holes 114, such that the liquid guided by the metal fiber element 8 can flow into the sleeve 6. The heating wire 7 is located inside the sleeve 6. When the heating wire 7 is heated by electricity, the liquid is vaporized and then passes through the smoke channel 106 and the inhalation hole 104 to be inhaled by a user. The atomizer 200 uses the metal fiber element 8 to guide the liquid to reach the heating wire 7 according to capillary principle, such that an improved atomizing effect can be achieved. In the illustrated embodiment, the heating wire 7 is made of nichrome. The atomizing cup 9 is made of polytetrafluoroethene, which is used as a bracket for the heating wire to avoid heat dissipation. The liquid conducting material 4 is capable of storing the tobacco flavored liquid temporarily according to capillary principle and can resist heat from conducting to container 100 effectively.

The nonwoven fabric 10 is sleeved on an end of the atomizing cup 9 away from the liquid tank 2. The nut 11 is positioned adjoining an end of the stainless steel pipe 5. The short pin 13 is received in the nut 11. The first washer 12, which is made of silicone, is positioned between the nut 11 and the short pin 13 to fix the short pin 13.

Figure 4:
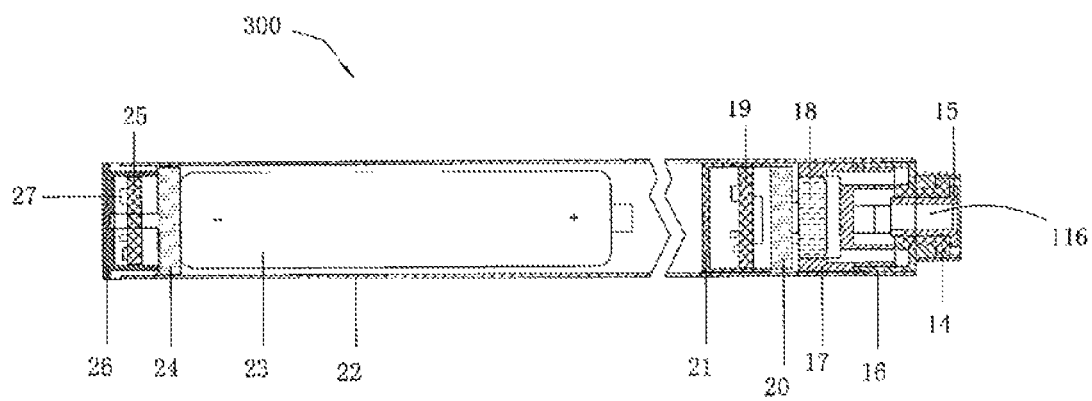
FIG. 4 is a cross-sectional view of a battery tube of the electronic cigarette of FIG. 1.

Referring to FIG. 4, the battery tube 300 includes a second washer 14, a second pin 15, a screw element 16, a switch seat 17, a switch 18, a control circuit board 19, a first insulation piece 20, an insulation cover 21, a tube body 22, a second insulation piece 24, a light control board 25, and a light cover 26. The screw element 16 is shaped as a substantially hollow cylinder and is engaged in the nut 11. The second pin 15 is located inside the screw element 16, and the second washer 14 is positioned between the screw element 16 and the second pin 15 to fix the second pin 15. The first pin 13 and the second pin 15 are both hollow components, and define a channel 116 therebetween communicating with the cavity 112. The screw element 16 is received in the tube body 22 via interference fit. The switch seat 17 is received in the tube body 22 adjoining the screw element 16. The switch 18 is received in the seat 17. The first insulation piece 20 is received in the tube body 22 adjoining the switch 18. The control circuit board 19 is positioned between the first insulation piece 20 and the insulation covering 21 and electrically connected to the heating wire 7. The switch 18 is configured to activate the control circuit board 19 to control a output current to the heating wire 7. The insulation cover 21 defines an opening (not labeled). The first insulation piece 20 is mounted on the insulation cover 21 to cover the opening. A battery 23 may be positioned between the insulation covering 21 and the second insulation piece 24 and be electrically connected to the control circuit board 19, The light cover 26 covers a end of the tube body 22 away from the atomizer 200. The light control board 25 is mounted between the second insulation piece 24 and the light cover 26 and electrically connected to the control circuit board 19. The battery tube 300 further includes a LED 27 positioned on the light control board 25.

Figure 5:
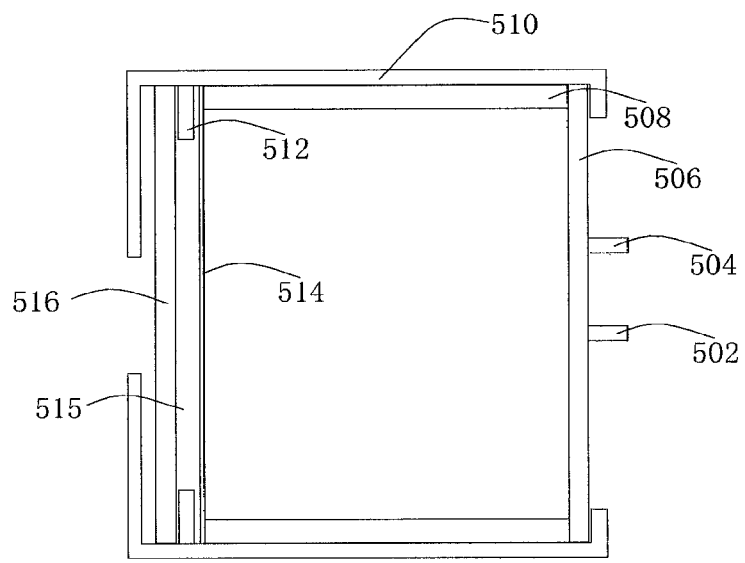
FIG. 5 is a side, schematic view of a switch of the electronic cigarette of FIG. 1 showing a actuating film is separated from a perforated plate.
Figure 6:
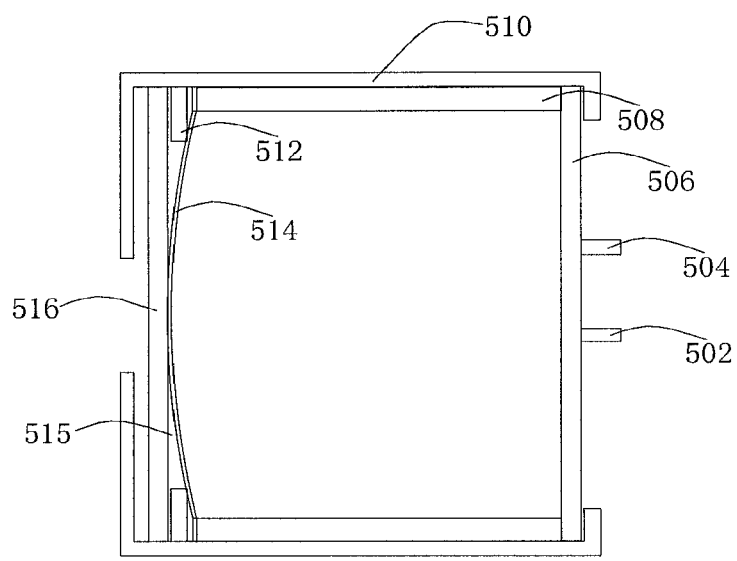
FIG. 6 is similar to FIG. 5, but shows the actuating film contacts the perforated plate.

Referring to FIG. 5 and FIG. 6, the switch 18 includes a negative electrode 502, a positive electrode 504, a printed circuit board (PCB) 506, a metal ring 508, an aluminum casing 510, an insulation plate 512, an actuating film 514, and a porous plate 516. The negative electrode 502 and the positive electrode 504 are located on the PCB 506. The PCB 506 is connected to the actuating film 514 via the metal ring 508. The perforated plate 516 is also connected to the PCB 506. The insulation plate 512 is positioned between the actuating film 514 and the perforated plate 516. The actuating film 514 and the perforated plate 516 cooperatively forms an unidirectional switch 515 When the actuating film 514 contacts the perforated plate 516 (as shown in FIG. 6), the unidirectional switch 515 is turned on, and the negative electrode 502 and the positive electrode 504 are coupled; when the actuating film 514 is separated from the perforated plate 516 (as shown in FIG. 5), the unidirectional switch 515 is turned off, and the negative electrode 502 and the positive electrode 504 are disconnected. The insulation plate 512 is positioned between the actuating film 514 and the perforated plate 516 to prevent the actuating film 514 from accidentally contacting the perforated plate 516. When the switch 18 is assembled in the electronic cigarette 400, the actuating film 514 is opposite to the cavity 112 and the channel 116, the perforated plate 516 is positioned between the actuating film 514 and the cavity 112. The perorated plate 516 is capable of allowing an airflow to pass through. When the cavity 112 is in a state of negative pressure, the actuating film 514 contacts to the perorated plate 516 and the switch is turned on. When the cavity 112 is in a state of positive pressure, the actuating film 514 is pushed away from the perorated plate 561 by the airflow and the switch cannot be turned on.

In use, the user inhales the electronic cigarette 400 at the inhalation hole 104, such that a negative pressure is formed inside smoke channel 106, cavity 112, and channel 116, and a pressure difference is formed on opposite sides of the actuating film 514. The actuating film 514 is therefore impelled to contact the perforated plate 516 by the pressure, and the negative electrode 502 and the positive electrode 504 are coupled to generate an electrical signal to activate a chip on the control circuit board 19 to power the heating element 7. The heating element 7 vaporizes the liquid conducted by the metal fiber element 8 into vapor, which is then inhaled by the user after passing through the channel 116, the cavity 112, the smoke channel 106 and the inhalation hole 104. Because the switch 18 has the unidirectional switch 515, it can stop the heating element 7 form working when the actuating film 514 is not under a negative pressure cooperating with the control circuit board 19. Therefore, no power consumption occurs when the electric cigarette stops working. The switch 18 is highly sensitive to a pressure differential created by inhaling airflow while is immune from an exterior noise. The LED 27 on the light control board 25 is turned on by the control circuit board 19 when the side of the actuating film 514 is in negative pressure condition, to imitate a lighting effect as a conventional cigarette.

The electronic cigarette 400 may be used as a substitute of conventional cigarette. Because the tobacco flavored liquid used by the electronic cigarette 400 doesn't contain nicotin, a damage to the user's health can be avoided. In addition, the electronic cigarette 400 can also reduce the cost of smoking and produce no cigarette ash and fire, and it is thus safe for use and good for environment protection.

It should be emphasized that the above-described embodiments of the present invention, particularly, any preferred embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. An atomizer assembly, comprising:
    a container defining a liquid storage cavity for receiving a liquid, the liquid storage cavity comprising a liquid outlet, an outlet-defining element positioned at the liquid outlet, and an absorbent element attached to an outside end of the outlet-defining element and covering an opening of the liquid outlet for preventing the liquid received in the liquid storage cavity from flowing out of the liquid storage cavity directly; wherein the outlet-defining element defines a shape and a size of the opening of the liquid outlet, and an atomizer connected to the container to atomize liquid permeating through the absorbent element by an electric heating element, wherein an area of the opening of the liquid outlet on an intersecting plane perpendicular to a longitudinal axis of the container is smaller than an area of a non liquid outlet portion of the liquid storage cavity on an intersecting plane perpendicular to the longitudinal axis of the container.

2. The atomizer assembly of claim 1, wherein the atomizer assembly comprises an inhalation end, and the liquid outlet is located at a side of the container away from the inhalation end.

3. The atomizer assembly of claim 1, further comprising an inhalation element comprising an inhalation end, wherein the liquid outlet is facing away from the inhalation end.

4. The atomizer assembly of claim 3, wherein the container defines an opening at an end thereof away from the inhalation end, the atomizer is inserted into the container through the opening at the end away from the inhalation end.

5. The atomizer assembly of claim 3, wherein the atomizer is closely attached to an inner sidewall of the container adjacent to the opening.

6. The atomizer assembly of claim 3, wherein the atomizer comprises an atomizing cup, and an end of the atomizing cup facing towards the liquid storage cavity is in contact with the absorbent element.

7. The atomizer assembly of claim 1, wherein the container defines an opening at an end thereof away from an inhalation end, the atomizer is inserted into the container through the opening at the end away from the inhalation end.

8. The atomizer assembly of claim 1, wherein the container defines a smoke channel extending along the longitudinal axis of the container, and the smoke channel is surrounded by the liquid storage cavity.

9. The atomizer assembly of claim 8, wherein the absorbent element surrounds the smoke channel.

10. The atomizer assembly of claim 8, wherein the container comprises an inhalation element and a liquid tank, the inhalation element is configured as a substantially hollow cylinder, the liquid tank is received in the inhalation element, the liquid tank defines the smoke channel, the atomizer comprises an atomizing cup, and an end of the liquid tank is received in the atomizing cup.

11. The atomizer assembly of claim 1, wherein the container is detachably connected to the atomizer.

12. The atomizer assembly of claim 1, wherein the absorbent element is an absorbent cotton.

13. The atomizer assembly of claim 1, wherein the container further comprises an inhalation element, and a liquid tank; the inhalation element is a substantially hollow cylinder defining an opening at one end and an inhalation hole at the other end thereof; the liquid tank defines a smoke channel in a middle portion thereof and in communication with the inhalation hole, the liquid tank is received in the inhalation element, the outlet-defining element is positioned at an end of the liquid tank; the inhalation element, the liquid tank and the absorbent element cooperatively define the liquid storage cavity to receive a liquid therein.

14. The atomizer assembly of claim 1, wherein the container comprises an inhalation element and a liquid tank; the liquid tank is received in the inhalation element and defines a smoke channel in a middle portion thereof, wherein the atomizer comprises a liquid conducting element, a stainless steel pipe, a sleeve, a heating wire, a metal fiber element, and an atomizing cup; the inhalation element, the stainless steel pipe, the liquid conducting element, the metal fiber element and the atomizing cup are coaxially arranged in that order; an end of the liquid conducting element and an end of the metal fiber element contact with the absorbent element, the atomizing cup defines a cavity communicating with the smoke channel; the atomizing cup defines a through hole; the sleeve is received in the cavity and aligned with the through hole.

15. An electronic cigarette, comprising:
a container defining a liquid storage cavity for receiving a liquid, the liquid storage cavity comprising a liquid outlet, an outlet-defining element positioned at the liquid outlet, and an absorbent element attached to and covering an opening of the liquid outlet for preventing the liquid received in the liquid storage cavity from flowing out of the cavity directly; wherein the outlet-defining element defines a shape and a size of the opening of the liquid outlet;
an atomizer connected to the container to atomize liquid permeating through the absorbent element by an electric heating element; and
a battery configured for powering the atomizer,
wherein an area of the opening of the liquid outlet on an intersecting plane perpendicular to a longitudinal axis of the container is smaller than an area of a non liquid outlet portion of the liquid storage cavity on an intersecting plane perpendicular to the longitudinal axis of the container.

16. An atomizer assembly, comprising:
a container comprising a liquid storage cavity for receiving a tobacco-flavored liquid, wherein the liquid storage cavity comprises a liquid outlet, wherein the container comprises:
an outlet-defining element that reduces a size of an opening of the liquid outlet; and
an absorbent element covering the opening of the liquid outlet; and
an atomizer for atomizing the tobacco-flavored liquid, when received in the liquid storage cavity, permeating through the absorbent element,
wherein the container is substantially elongated, and the outlet-defining element reduces an area of the opening of the liquid outlet such that an area of the opening of the liquid outlet on an intersecting plane perpendicular to a longitudinal axis of the container is smaller than an area of a non liquid outlet portion of the liquid storage cavity on an intersecting plane perpendicular to the longitudinal axis of the container.

17. The atomizer assembly of claim 16, wherein the absorbent element is in contact with the outlet-defining element.

18. The atomizer assembly of claim 16, wherein the outlet-defining element reduces an area of the opening of the liquid outlet such that the opening is smaller in size than that of a non liquid outlet portion of the liquid storage cavity.

* * * * *